United States Patent [19]

Szonntagh

[11] 4,306,451
[45] Dec. 22, 1981

[54] GAS ANALYZER

[75] Inventor: Eugene L. Szonntagh, Flourtown, Pa.

[73] Assignee: Honeywell Inc., Minneapolis, Minn.

[21] Appl. No.: 143,278

[22] Filed: Apr. 24, 1980

[51] Int. Cl.³ ............................................. G01N 25/30
[52] U.S. Cl. ............................................... 73/190 CV
[58] Field of Search .................................. 73/190 CV

[56] References Cited

U.S. PATENT DOCUMENTS

| 1,134,768 | 4/1915 | Smith | 73/190 CV |
| 3,393,562 | 7/1968 | Breedlove | 73/190 CV |
| 3,521,480 | 7/1970 | Cropper et al. | 73/36 |

Primary Examiner—Charles A. Ruehl
Attorney, Agent, or Firm—Laurence J. Marhoefer; Lockwood D. Burton; Mitchell J. Halista

[57] ABSTRACT

A gas analyzer for determining the BTU or caloric content of a combustible gas uses a temperature measuring device for measuring the temperature of a metal cup which is heated by a flame produced by the combustion of the gas in an excess air environment. The supply of combustible gas is periodically turned off while the air supply flow is maintained to produce a periodic heating and cooling sequence of the metal cup during fixed respective time periods. A differential temperature monitor is arranged to monitor the temperature of the metal cup and the incoming fuel and air to produce a differential temperature signal during the heating and cooling sequence. In a second embodiment, the gas flame is continuously ignited and is supplied from a rotating gas jet in the excess air environment. The flame is sequentially applied to a series of metal cups to produce a heating and cooling sequence of each cup. The temperature of each cup and the incoming gas and air is monitored by a differential temperature monitor to produce a differential temperature output for the heating and cooling sequence for each cup. A representation of the caloric content of the gas can be obtained either by a solution of a caloric content equation based on the differential temperature obtained by the heating or by an analysis of the temperature waveshape of the heating and cooling sequence for either the individual cup or the plurality of cups.

7 Claims, 4 Drawing Figures

GAS ANALYZER

BACKGROUND OF THE INVENTION

1. Field of the Invention

The present invention relates to gas analyzers. More specifically, the present invention is directed to a gas analyzer for determining the caloric content of a combustible gas.

2. Description of the Prior Art

The measurement of the BTU, or caloric, content of a combustible gas such as that supplied for home heating, etc., can provide a measure of the quality of the gas being supplied and, hence, serve as a basic for an appropriate rate or cost for the gas to be used for billing a customer who formerly was charged a rate based simply on cubic volume of gas consumption. Conventional gas analyzers for determining the composition of an unknown gas are well-known in the art. One such analyzer is known as the Orsat type and is used to absorb the constituent gases one at a time from a gas mixture and to determine the constituent gas quantities from the resulting decreases in the gas pressure. While the resulting gas analysis could be used as a basis for customer billing, such an apparatus is wholly impractical for mass installation directly in gas consumer locations. Another type of prior art gas analyzer is based on the use of thermal conductivity of the unknown gas which gas is analyzed by comparing its rate of thermal conductivity with that of a standard reference gas. Still another type of prior art gas analyzing device has used various arrangements of a catalyzing wire, e.g., platinum which has its temperature affected by the gas being burned adjacent to the wire to produce an output signal which is used to ascertain the percentage of combustible gas in the gas being tested. Still another group of prior art gas analyzers were based on an optical analysis, e.g., color, etc., of gas flame in the variety measure of combustible gas content. A recent development has used a gas flame fueled by the gas being tested to achieve a maximum flame temperature while monitoring the flow rate of the gas and air supplying the flame. All of these prior art devices have serious shortcomings in providing a rapid and accurate measure of the BTU content of the combustible gas while utilizing a compact and simple structure suitable for mass production and capable of being mounted in unattended customer locations. Accordingly, it is desirable to provide a BTU meter capable of determining the BTU or caloric content of an unknown gas composition to provide an accurate measure of the billing cost to be assigned to the gas during a sale of the gas to a consumer.

SUMMARY OF THE INVVENTION

An object of the present invention is to provide an improved gas analyzer for determining the caloric content of a combustible gas.

In accomplishing this and other objects, there has been provided, in accordance with the present invention, a gas analyzer having means for monitoring the temperature cycle produced by the combustion in an excess air mixture of a gas to be analyzed using a constant gas and air flow and by a periodic interruption of the combustion to produce a heating and cooling pattern which is analyzed to provide a measure of the relative caloric content of the gas to be analyzed. The analysis can be either a direct waveshape analysis or a solution of a caloric content equation utilizing the temperatures attained.

BRIEF DESCRIPTION OF THE DRAWINGS

A better understanding of the present invention may be had when the following detailed description is read in connection with the accompanying drawings, in which.

DETAILED DESCRIPTION OF THE PREFERRED EMBODIMENT

Figure 1:
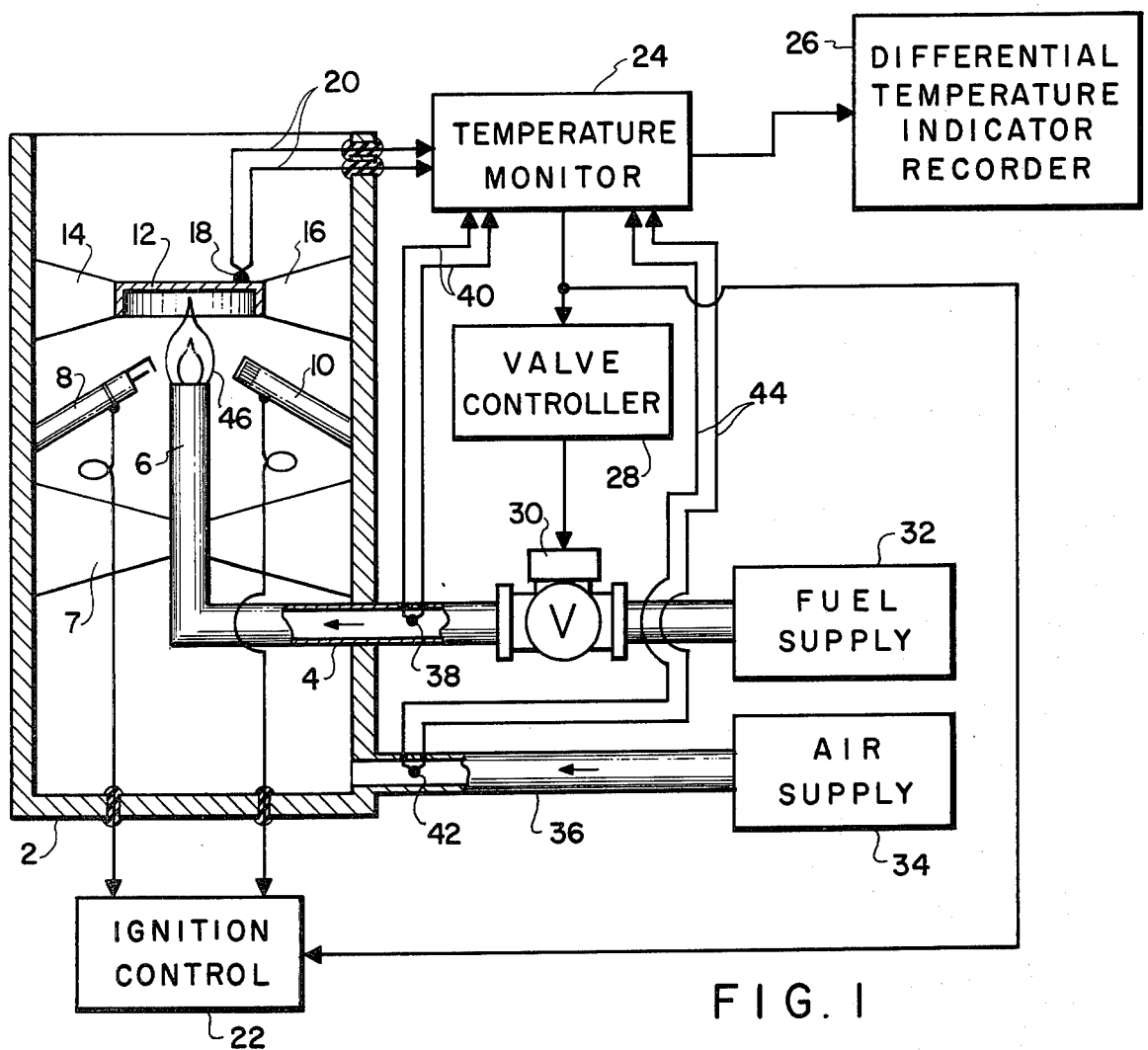
FIG. 1 is a block diagram of a gas analyzer embodying a first example of the present invention.

Referring to FIG. 1 in more detail, there is shown a gas analyzer having an open top gas combustion chamber 2. The combustion chamber 2 has a gas pipeline 4 passing through a wall of the chamber 2 and terminating in a gas jet 6 centrally supported and spaced from the wall of the chamber 2 by a pair of support fins 7. A gas igniting spark is produced by a conventional gas ignitor 8 attached to the inner wall of the chamber 2 and having a spark producing element adjacent to the gas jet 6. A flame sensor 10 is provided adjacent to the gas jet 6 and may be any suitable device arranged to produce an output signal indicative of the presence of a gas flame at the gas jet 6 such devices being well-known in the art. A cup 12 which functions as a "mini-calorimeter" is suspended by thermally isolating fins 14 and 16 from the interior wall of the chamber 2 adjacent to the gas jet 6. The cup 12 may be made of any suitable material, e.g., metal, ceramic, etc., capable of withstanding the temperature of the gas flame. The gas jet 6 is located on one side of the cup 12 while a first temperature sensing device 18, e.g., a thermistor, a thermocouple, etc., is located on the other side of the cup and in contact therewith to measure the temperature of the cup 12 and to produce a corresponding output signal on an output line 20. An ignition control 22 is arranged to control the ignition of the gas flame at the gas jet 6 by the ignitor 8 and to receive a signal from the gas flame sensor 10 to monitor the presence of the gas flame at the gas jet 6 to produce the intermittent combustion of the gas at the gas jet 6 as previously mentioned.

The output signal from the temperature sensing device 18 on the output line 20 is applied to an input of a temperature monitor 24. The temperature monitor 24, in turn, produces an output signal which is applied to a temperature recorder indicator 26. A temperature monitor 24 may be any suitable prior art device for producing an output signal which is the difference between input signals being monitored thereby, such signal monitors being well-known in the art. The temperature monitor 24 also includes a timer which is used to produce a periodic control signal for controlling a valve controller 28 and the ignition control 22. The valve controller 28, in turn, is arranged to use the timer control signal from the temperature monitor 24 to selectively operate a control valve 30. The control valve 30 is arranged to control gas being supplied from a constant pressure supply 32 to the pipeline 4. A constant flow air supply 34 is used to supply air to the combustion chamber 2 via a pipeline 36.

A second temperature sensing element, e.g., thermistor 38, is located within the pipeline 4 to measure the temperature of the gas from the control valve 30 and to produce a corresponding output signal on signal line 40 which is connected to a respective input of the temperature monitor 24. Similarly, a third temperature sensing element, e.g., thermistor 42, is located in the pipeline 36 to measure the temperature of the incoming air and to produce a corresponding output signal on an output line 44 which is also connected a respective input of the temperature monitor 24. The output signals from the thermistors 38, 42 provide correction signals for the differential temperature output signal from the temperature monitor 24 as supplied to the indicator recorder 26. The temperature indicator recorder 26 may include a recorder or other devices to provide a visual indication and/or a record of the heating and cooling cycle of the cup 12 which is the measure of the caloric content of a gas being intermittently burned at the gas jet 6.

Figure 2:
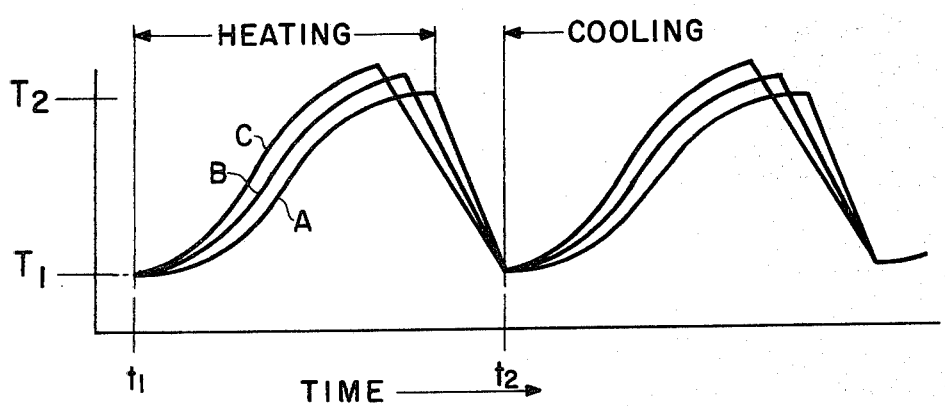
FIG. 2 is a waveshape diagram of heating and cooling cycles produced by the analyzer shown in FIG. 1.

In operation, the valve 30 is initially opened by the valve controller 28 in response to the control signal from the timer in the monitor 24. The gas to be analyzed is then admitted to the pipeline 4 and is ignited at the gas jet 6 by the ignitor 8 controlled by the ignition control 26 in response to the timer control signal to produce a gas flame 46. The gas flame 46 is effective to heat the cup 12 to a temperature as determined by the air/fuel ratio being supplied to the gas flame 45. The constant flow air supply from the air supply 34 is maintained at an excess air condition for the gas being analyzed to insure complete combustion thereof while the fuel gas is supplied at a predetermined constant flow rate from the gas supply 32. The aforesaid temperature of the cup 12 is sensed by the first temperature sensing device 18 to produce a corresponding output signal to the temperature monitor 24. The temperature monitor 24, in turn, produces a first output signal indicative of the differential temperature being monitored between the heated cup 12 and the incoming gas in pipeline 4 as corrected by the temperature of the incoming air in pipeline 36. This differential temperature output signal from the monitor 24 is indicative of the heating of the cup 12 by the flame 46. This first differential temperature signal is recorded by the indicator recorder 26 as is shown in FIG. 2 under the "heating" portion of the temperature change cycle.

After a predetermined time as determined by the timer in the temperature monitor 24, the control valve 30 is closed by the control signal applied to the valve control 28 from the timer in the monitor 24. The cup 12 is then in a cooling cycle as shown in FIG. 2 under the "cooling" portion of the temperature change cycle. The cup 12 is cooled by the continuing passage of air through the combustion chamber 2 from the air supply 34. After a cooling period for a predetermined time as controlled by the timer in the monitor 24, the above heating and cooling cycle is repeated. The differential temperature achieved by the heating and cooling cycle is between the temperature attained by the cup 12 as corrected by the temperature of the incoming fuel gas and the temperature of the incoming air as corrected by the temperature of the incoming fuel gas. This temperature differential can be recorded by the indicator recorder 26 as representative of a relative calorific value of the gases being tested. A more accurate determination of the calorific value than is possible with the above method can be obtained by considering the heating and cooling portions to be separate curves and using well-known waveshape analysis techniques to obtain information related to calorific value of the combustible gas. Several known methods are Fourier analysis, real-time spectrum analysis and super-heterodyne or super-toned analysis as discussed in "Van Nostrand's Scientific Encyclopeida" (5th Edition, 1976) under the heading "Spectrum Analysis". A specific example of using Fourier analysis for heat flow equations is shown in "Fourier Series and Boundary Value Problems" by R. V. Churchill on pages 17 to 20, published by McGraw-Hill, 1941.

Alternatively, using the data provided by the gas analyzer of the present invention, the conventional caloric equation can be solved to derive an actual calorific value of the gas. This equation, as shown on page 175 of "Heat and Temperature Measurement" by Weber (1950), is:

$$Q = Q_1 + k \int_{t_1}^{t_2} (T - T_{air}) \, dt - Q_2 \text{ where:}$$

Q is the caloric value of the gas to be analyzed
$Q_1$ is the specific heat $\times$ mass $\times$ temperature gradient of the cup 12
K is the thermal leakage modulus
T is the highest temperature attained by the cup 12
$T_{air}$ is the temperature of the incoming air as corrected by the temperature of the incoming gas
t is time in seconds
$Q_2$ is the additional heating or cooling caused by nearby devices.

The gas analyzer of the present invention can be calibrated by using a reference gas flame to determine the $Q_1$, $Q_2$ and K in the above equation which can be subsequently solved for the unknown gas being analyzed. A digital computer system (not shown) could be used to facilitate the solution of the aforesaid equation and would include well-known elements such as analog-to-digital converters, memory, etc. This system could be located in the monitor 24, and the indicator recorder 26 could be used to record digital values of the caloric content. Further, the gas analyzer system could include a telemetering apparatus having a signal transmitter/receiver (not shown) for communicating the caloric value obtained by the gas analyzer of the present invention with a central billing facility for providing gas analysis data to determine the customer's billing rate.

Figure 3:
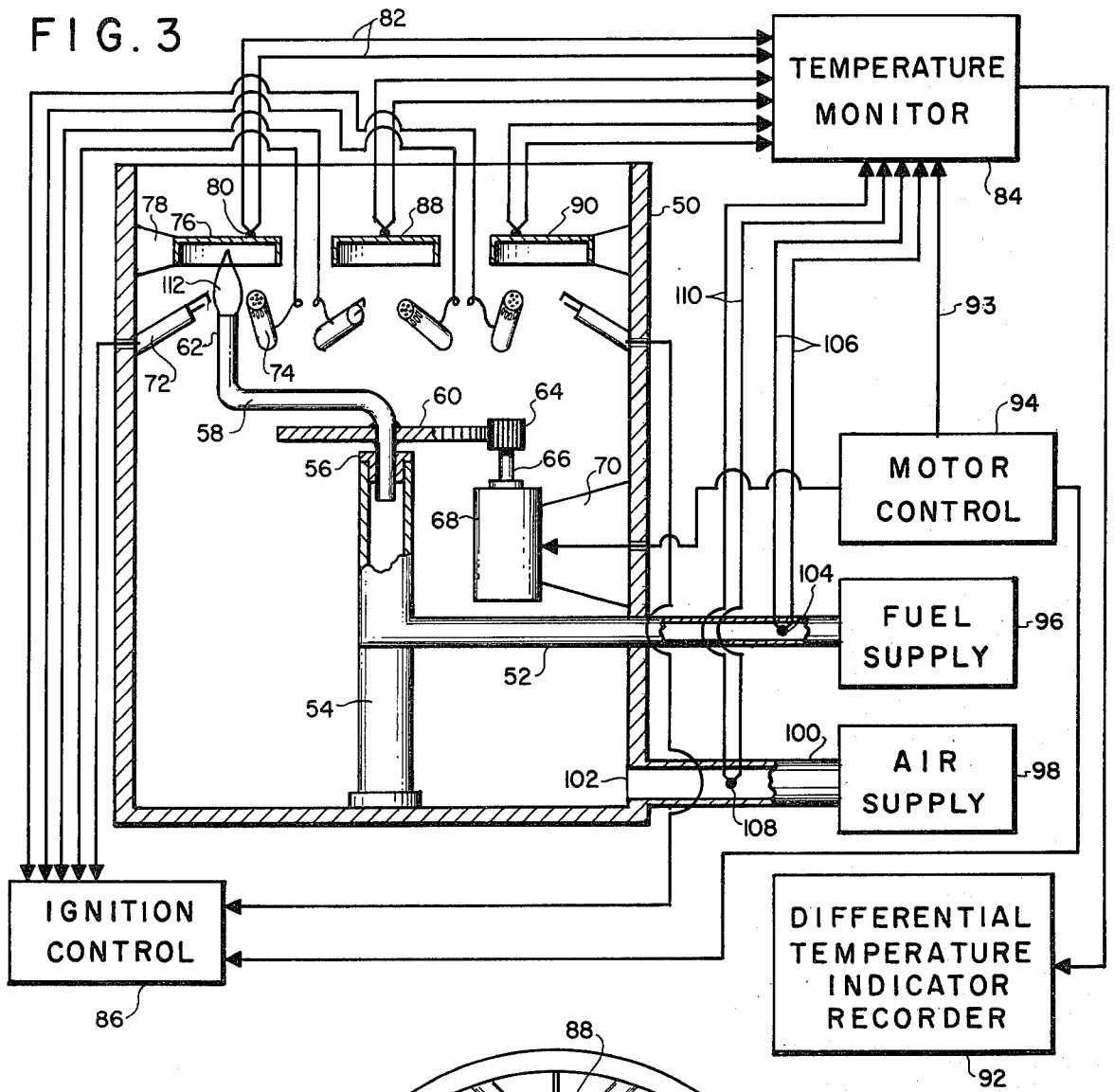
FIG. 3 is a block diagram of a gas analyzer embodying a second example of the present invention.

Referring to FIG. 3 in more detail, there is shown a gas analyzer embodying a second example of the present invention and utilizing an open top combustion chamber 50. The combustion chamber 50 has a gas pipeline 52 passing through a wall of the chamber 50 and being attached to a centrally located stationary support 54. The pipeline 52 terminates in a rotary seal 56 arranged to seal the peripheral surface of one end of a gas jet tube 58. The gas jet tube 58 is passed through the center of a gear 60 and is attached thereto. The gas jet tube 58 is shaped in the form of crank arm and has an output port 62 at the other end of the tube 58. The gear 60 is arranged to be driven by a spur gear 64 axially attached to the output shaft 66 of a drive motor 68. The motor 68 is supported by a support fin 70 on the inner wall of the combustion chamber 50. A gas ignitor 72 having a spark producing element is mounted on the inner wall of the chamber 50 and is arranged to have the spark producing element adjacent to the gas jet 62. A flame sensor 74 is also mounted on the inner wall of the chamber 50 adjacent to the gas jet 62 to produce an output signal indicative of the presence of a gas flame at the gas jet 62. A first cup 76, e.g., metal, ceramic, etc., which functions as a mini-calorimeter is suspended by a thermally isolating fin 78 from the inner wall of the combustion chamber 52 and is located above the gas jet 62. The gas jet 62 is located on one side of the cup 76 while a temperature sensing device 80, e.g., a thermistor, a thermocouple, etc., is located on the other side of the cup 76 and in contact therewith to measure the temperature of the cup 76. The temperature sensing device 80 has an output signal line 82 which is connected to an input of a temperature monitor 84. The gas ignitor 72 and the flame sensor 74 are connected to an ignition control 86 which is arranged to control the ignition of the gas flame at the gas jet 62 by the ignition element 72 while receiving a signal from the gas flame sensor 74 to monitor the presence of the gas flame at the gas jet 62.

Additional cups, e.g., cups 88 and 90 are arranged on the circumference of the circle described by the gas jet 62 during rotation of the gas tube 58 by the gear 60. Each of the additional cups 88 and 90 is also associated with a gas ignitor and a flame sensor which are, in turn, connected to the ignition control 86 to control and monitor the ignition of the gas flame at a corresponding ones of the additional cups 88 and 90. Further, each of the additional cups 88, 90 is associated with a temperature sensor. The output signals from temperature sensing devices located on each of the additional cups 88 and 90 are connected to the temperature monitor 84. The temperature monitor 84, in turn, has an output signal which is indicative of the temperature of the cups 88 and 90 as each cup is heated in turn by the gas flame at the gas jet 62. This output signal from the temperature monitor 84 is sequentially supplied to a differential temperature indicator 92. The temperature monitor 84 may be any suitable prior art device, as previously discussed, for producing an output signal which is a difference between output signals being monitored thereby, such signal monitors being well-known in the art. The temperature monitor 84 may include a signal multiplexer for sequentially utilizing each of the output signals from the temperature sensing elements associated with the cups 76, 88 and 90. Such a signal multiplexer would have its operation synchronized with the operation of the motor 68 by means of a timing signal supplied on a timing signal line 93 from a motor control 94 which is also arranged to energize the drive motor 68.

A fuel supply 96 is arranged to supply a constant flow of the combustible gas to be measured to the pipeline 52. An air supply 98 is arranged to supply a constant supply of air via a pipeline 100 passing through the wall of the chamber 50 and terminating in an exit port 102 within the combustion chamber 50. A temperature sensing element, e.g., thermistor 104, is located within the pipeline 52 to measure the temperature of the incoming gas from the fuel supply 96 and to produce a representative output signal on an output line 106 which is connected to an input of the temperature monitor 84. Similarly, a second temperature sensing element, e.g., thermistor 108, is located within the pipeline 100 to measure the temperature of the incoming air and to produce a representative output signal on an output line 110 which is connected to an input of the temperature monitor 84. The thermistors 104 and 108 provide correction signals to the temperature monitor 84 which are used to determine differential temperature output signal, as previously discussed, from the temperature monitor 84 as supplied to the indicator recorder 92. The indicator recorder 92 may include a recorder or other devices to provide a visual indication and/or a record of the heating and cooling cycle of each of the cups 76, 88 and 90, as shown in FIG. 2 and discussed above, as a measure of the caloric content of the gas being burned at the gas jet 62.

Figure 4:
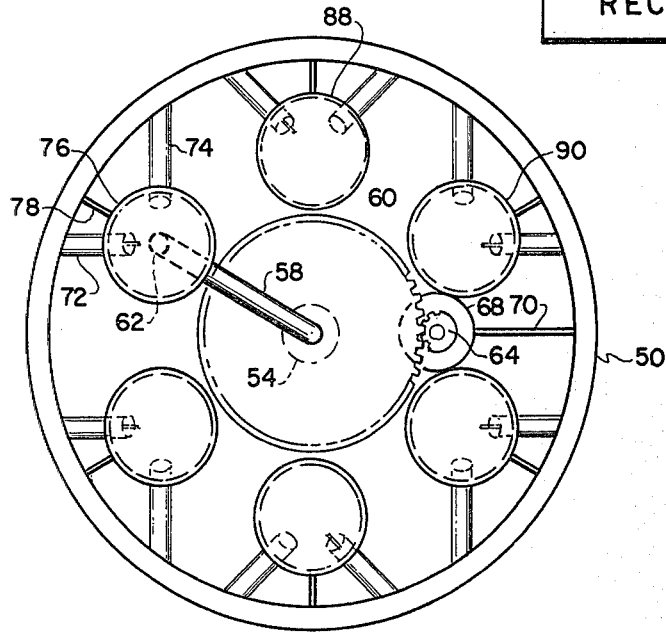
FIG. 4 is a top view of the combustion chamber used in the analyzer shown in FIG. 3.

In FIG. 4, there is shown a top view of the combustion chamber 50 to illustrate the relative location of the parts therein. The number of cups, spark producing elements and flame sensors is shown in a greater number in FIG. 4 than the three element structure illustrated in FIG. 3 since the number of these elements may be increased or decreased without departing from the present invention. Similar reference numbers have been used in FIG. 4 to correlate the structure with the elements illustrated in FIG. 3.

In the operation of the gas analyzer shown in FIG. 3, the incoming gas is initially ignited at the gas jet 62 by the ignition control 86 to produce a gas flame 112. The gas flame 112 is effective to heat an adjacent cup, e.g., cup 76, to a temperature as determined by the air/fuel ratio being supplied to the gas flame 112 with the air supply from the air supply 98 being maintained at an excess air condition for the gas being analyzed to insure complete combustion thereof. This temperature of the cup is sensed by the temperature measuring device associated therewith, e.g, temperature measuring device 80, to produce an output signal to the temperature monitor 84. The temperature monitor 84, in turn, produces an output signal indicative of the differential temperature between the cup 76 and the temperature of the incoming gas and air as monitored by thermistors 104 and 108 to produce an output signal indicative of the relative caloric content of the gases being tested. After a predetermined time which insures the attainment of a maximum temperature of the cup 76, the motor drive 94 is arranged to energize the drive motor 68. The gas jet 62 is driven by the drive motor 68 to a position between the cup 76 and the next cup 88 is retained in this position for a predetermined time. This allows a cooling of the first cup 76 to occur.

Subsequently, the gas jet 62 is positioned beneath the second cup 88 by the energization of the motor 68 by the motor control 94. Concurrently, a timing signal is applied to the timing line 93 by the motor control 94. This timing signal is effective to advance the signal multiplexer in the temperature monitor 84 whereby the output signal from the thermistor associated with the second cup 88 is connected to utilization by the temperature monitor 84. The second cup 88 is now heated by the flame 112 for a predetermined period of time for a repetition of the cycle described above with respect to cup 76. The timing of the movement of the gas 62 can be based on any suitable time period, e.g., four seconds under a cup and four seconds between the cups. In any case, sufficient cooling time must be allowed to enable the same end temperature to be attained by all gases being tested. Using this four second time frame, a calorific value can be obtained from the monitor 84 every eight seconds. The analysis of each of the input signals to the monitor 84 can be performed as described above with respect to the operation of the analyzer shown in FIG. 1. The use of the caloric equation would require a calibration of the gas analyzer shown in FIG. 3 by using a reference gas flame to determine the $Q_1$, $Q_2$ and K of each of the cups.

While the preceding discussion of the operation of the gas analyzer of the present invention used a timing cycle for the rotation of the gas jet 62 which included a pause between the cups, a signal sampling or time sharing arrangement of the temperature signals would enable the gas jet 62 to simply continue to the next cup without a between cup pause while the temperature of the cup would be sequentially sampled at an appropriate period, e.g., every fifty milliseconds. Such a sampling of the temperature data could be achieved by well-known conventional means, and the resulting samples stored and analyzed by a digital computer. Additionally, while the exemplary structure of the gas analyzer embodying the present invention has been presented in an arrangement utilizing a constant pressure gas supply, the temperature measurement could be compensated for a varying gas flow by measuring the actual gas flow and supplying the flow data to a data processing system, e.g., a digital computer, to modify the temperature measurements in accordance therewith. Similarly, a compensation for a varying air flow could be effected in the temperature measurements by utilizing the cooling curve data obtained during a reference or calibration operation of the gas analyzer wherein the air flow is constant whereby the cooling curve measurements for different or varying air flows could be modified by a data processor based on the deviation from the reference cooling curve. In any case, the amount of air is always maintained to provide an excess air environment for the gas combustion. Finally, while a movement of the gas jet 62 has been shown in the example of the invention shown in FIG. 3, it is obvious that a modification of the structure could have the gas jet 62 stationary and the cups 76, 88 and 90 moved past the flame. On the other hand, in still another modification, the gas jet 62 and the cups 76, 88 and 90 could both be stationary and the gas flame 112 could be physically diverted to each cup in succession by a constant pressure air jet selectively directed at the flame 112. Other modifications of the structure disclosed herein may occur to those skilled in the art without departing from the spirit and scope of the claimed invention.

Accordingly, it may be seen that there has been provided, in accordance with the present invention, an improved gas analyzer for rapidly and accurately determining the caloric content of a combustible gas.

The embodiments of the invention in which an exclusive property or privilege is claimed are defined as follows:

1. A gas analyzer comprising
    combustion means for producing combustion of a gas to be analyzed in an excess air environment,
    a body arranged to be heated by said combustion of the gas to be analyzed,
    temperature detecting means for producing an output signal representative of a temperature in said body,
    means for periodically interrupting the heating of said body after a first predetermined time period to allow a cooling of said body for a second predetermined time period and
    means for analyzing the temperature of said body during said first and second time periods to determine a representation of a relative calorific value of said gas.

2. A gas analyzer as set forth in claim 1 wherein said means for periodically interrupting includes drive means arranged to selectively displace said combustion means with respect to said body to produce said heating and cooling of said body.

3. A gas analyzer as set forth in claim 1 wherein said means for periodically interrupting includes valve means controlling the flow of the gas to be analyzed and valve control means for periodically operating said valve means between an open state during said first time period and a closed state during said second time period.

4. A gas analyzer as set forth in claim 1 wherein said means for analyzing includes first means for measuring the temperature of said gas to be analyzed, second means for measuring the temperature of said air supplied to said combustion means and third means for correcting said output signal from said temperature detecting means in response to output signals from said first and second means.

5. A method for determining the calorific value of a combustible gas including the steps of producing a combustion of the gas in an excess air mixture of gas and air, applying a flame produced by the combustion to raise the temperature of a heat-absorbing body, interrupting the application of the flame to the body, monitoring the heating and cooling of the body by the application and interruption of the flame thereto, correcting the heating and cooling temperatures by the temperatures of the gas and the air used for the combustion and analyzing the corrected temperatures as a representation of the relative calorific value of the combustible gas.

6. A method as set forth in claim 5 wherein the step of analyzing the corrected temperatures includes the step of recording the waveshape of the heating and cooling process of the body.

7. A method as set forth in claim 5 and including the further steps of introducing a reference gas to produce the flame and using the temperature produced thereby to derive data for use in solving the following caloric equation, $$Q = Q_1 + K \int_{t_1}^{t_2} (T - T_{air}) \, dt - Q_2$$

where
    Q is the caloric value of the gas to be analyzed,
    $Q_1$ is the specific heat × mass × temperature gradient of the body,
    K is the thermal leakage modulus
    T is the highest temperature attained by the body
    $T_{air}$ is the incoming air temperature as corrected by the temperature of the incoming gas
    t is time in seconds,
    $Q_2$ is the additional heating or cooling provided by nearby devices.

* * * * *